(12) United States Patent
Wan et al.

(10) Patent No.: US 12,127,573 B2
(45) Date of Patent: Oct. 29, 2024

(54) HIGH-VOLTAGE ELECTRIC FIELD LOW-TEMPERATURE PLASMA COLD STERILIZATION SYSTEM CIRCUIT AND APPARATUS

(71) Applicant: NANJING SUMAN PLASMA TECHNOLOGY CO., LTD., Nanjing (CN)

(72) Inventors: Lianghao Wan, Nanjing (CN); Jun Yao, Nanjing (CN); Long Xu, Nanjing (CN); Jinglin Wan, Nanjing (CN)

(73) Assignee: NANJING SUMAN PLASMA TECHNOLOGY CO., LTD., Nanjing (CN)

( * ) Notice: Subject to any disclaimer, the term of this patent is extended or adjusted under 35 U.S.C. 154(b) by 604 days.

(21) Appl. No.: 17/613,768

(22) PCT Filed: Oct. 11, 2021

(86) PCT No.: PCT/CN2021/122952
§ 371 (c)(1),
(2) Date: Nov. 23, 2021

(87) PCT Pub. No.: WO2022/100328
PCT Pub. Date: May 19, 2022

(65) Prior Publication Data
US 2023/0148634 A1    May 18, 2023

(30) Foreign Application Priority Data
Nov. 13, 2020 (CN) .......................... 202011270523.X

(51) Int. Cl.
*A23L 3/32* (2006.01)
*A61L 2/14* (2006.01)
*A61L 2/26* (2006.01)

(52) U.S. Cl.
CPC .................... *A23L 3/32* (2013.01); *A61L 2/14* (2013.01); *A61L 2/26* (2013.01); *A61L 2202/24* (2013.01)

(58) Field of Classification Search
CPC ..... A23L 3/32; A61L 2/14; A61L 2/26; A61L 2202/24; A47J 31/41; A47J 31/4485;
(Continued)

(56) References Cited

U.S. PATENT DOCUMENTS

| | | | | |
|---|---|---|---|---|
| 5,397,961 A | * | 3/1995 | Ayers | A61L 2/14 |
| | | | | 210/243 |
| 2007/0125768 A1 | * | 6/2007 | Kim | H05B 6/062 |
| | | | | 219/626 |

FOREIGN PATENT DOCUMENTS

CN    109947074 A    6/2019

* cited by examiner

*Primary Examiner* — Phuong T Nguyen

(57) ABSTRACT

The present invention discloses a high-voltage electric field low-temperature plasma cold sterilization system circuit and apparatus, and belongs to the field of frequency converter power source circuit technologies. The present invention including a power source module, a voltage/current/power adjustment module, a switch module, and a transformer module. The power source module includes a single-phase frequency converter and a first-stage inductance. An inductance is connected in series between the output end of the frequency converter and a voltage regulator, to play a role of a reactor, harmonic components in sine pulse width modulation waves outputted by the frequency converter are effectively restrained, and spectrum is expanded, so that a harmonic current entering the voltage adjustment module is stable, and heat losses of the voltage adjustment module are reduced to prevent burnout

10 Claims, 3 Drawing Sheets

(58) Field of Classification Search
CPC . A47J 2203/00; B67D 1/0871; B67D 1/0884; B67D 1/12
USPC ......... 99/451, 452, 453, 455, 456, 470, 516, 99/517
See application file for complete search history.

HIGH-VOLTAGE ELECTRIC FIELD LOW-TEMPERATURE PLASMA COLD STERILIZATION SYSTEM CIRCUIT AND APPARATUS

TECHNICAL FIELD

The present invention relates to the field of frequency converter power source circuit technologies, and more specifically, to a high-voltage electric field low-temperature plasma cold sterilization system circuit and apparatus.

BACKGROUND

Plasma is a fourth state of material existence. The plasma is formed by ionized conductive gas, which includes six types of typical particles, namely, electrons, positive ions, negative ions, atoms or molecules in an excited state, atoms or molecules in a ground state, and photons.

Ions, electrons, atoms and molecules in an excited state, and free radicals enriched in a low-temperature plasma space are all active particles, and can react with surfaces of materials easily. Therefore, the plasma is widely applied to fields such as sterilization, surface modification, thin film deposition, etching processing, and device cleaning.

High-voltage electric field low-temperature plasma cold sterilization is a new food cold sterilization technology in the world currently. In 2009, the Purdue University of US initiates a research, to reach a sterilization effect by exciting medium gas around food to generate photoelectrons, ions, and reactive free radicals to come in contact with surfaces of microbes so as to damage cells of the microbes. In 2012, the academy of agricultural science of the United States Department of Agriculture (QSARU, USDA-ARS) starts to research and develop dielectric barrier discharge-based low-temperature plasma cold sterilization experimental apparatus, researches cold sterilization fresh-keeping performance characteristics of fresh chicken, and achieve a good sterilization effect in fresh food such as fresh meat. In recent 3 years, Japan and South Korea also start to research low-temperature plasma cold sterilization technologies. However, research about cold sterilization on high-voltage electric field low-temperature plasma food in the world is still limited to a laboratory research stage of sterilization performance characteristics and mechanism thereof currently.

A plasma sterilization technology is a new-generation high-tech sterilization technology, which can overcome some limitations and defects in existing sterilization methods, to improve disinfection and sterilization effects.

Compared with the currently widely used thermal sterilization technology, the low-temperature plasma cold sterilization technology is an important breakthrough of a food cold sterilization fresh-keeping packaging technology. Performing sterilization processing on packaging products may not generate secondary pollution. Plasma come from gas inside a package, so that no chemical residues may not be generated so as to achieve high security. Although a used voltage is quite high, a current is relatively small, a sterilization process is relatively short and no heat is generated, and power consumption is relatively low and operations are easy. Therefore, as a new cold sterilization manner, the high-voltage electric field low-temperature plasma cold sterilization is particular suitable for cold sterilization on heat-sensitive food (for example, fresh meat products of meat, poultry, and fish and prepared foods, fresh fruits and vegetables, and fresh-cut vegetables).

A proportion of fresh prepared food in market consumption becomes increasingly large, which is wasted seriously due to a short shelf life. The conventional commercial sterilization technologies greatly influence flavors, colors, and sensory qualities of fresh products, and as an international newly emerged non-thermal sterilization technology, the high-voltage electric field low-temperature plasma cold sterilization has advantages such as efficient automation, cold sterilization with no residue, low carbon, and environmental protection.

This technology can be also applied to disinfection and sterilization processing on products on production lines. A low-temperature plasma includes charged particles, high-energy electrons, and electrically neutral reactive particles such as free radicals, and atoms and molecules in an excited state. Plasma is generated due to high voltage discharge, and reflects a quick and efficient sterilization capability when reacting with microbes along with complex physicochemical effects. In addition, the reactive particles in the plasma may be adsorbed by materials quickly after coming into contact with the materials, and play a role of sterilization continuously on the materials after being adsorbed. Therefore, this technology is the most promising sterilization and disinfection technology currently, and has a wide application prospect in fields such as environment, biology, and medical care.

With the popularization of frequency converter technologies, applications of frequency converters also become increasingly wide, and a mainly involved field is a basic power source for speed adjustment of a motor, to meet a requirement of speed adjustment of the motor. However, a frequency converter is formed by alternating current-direct current-alternating current (a modulation wave) circuits, and a wave shape of an output voltage is a pulse square wave, and a proportion of harmonic waves is relatively large. Voltages and frequencies change proportionally at the same time, and cannot be adjusted separately. Under general, a function thereof is an electrical power control device that controls an alternating current motor by changing frequency of a working power source of the motor, and is not suitable for serving as a power source driving power to discharge. However, an expanded field as a power source circuit thereof cannot be widely applied currently.

For example, in a Chinese invention patent application entitled "DSPACE-BASED FAULT DIAGNOSIS PLATFORM FOR SHIP SHORE POWER SYSTEM" (application number: 201910052776.0, and application date: Jan. 21, 2019), the application discloses a shore power system unit, and the shore power system unit includes an alternating current power source, a transformer, a frequency converter, a filtering apparatus, a power compensation apparatus, a grid-connection apparatus, and a breaker, where the filtering apparatus used is a capacitor. A filtering external characteristic of the capacitor is relatively poor, when there is current impact, and in particular in a start-stop stage, circuit overload may be caused subsequently, and the circuit may be damaged.

SUMMARY

Technical Problem

An objective of the present invention is to overcome a defect in the existing technologies that a frequency converter can only carry inductive loads but cannot drive capacitive loads. A high-voltage electric field low-temperature plasma cold sterilization system circuit is provided, where an output frequency and voltage of a power source module are adjustable, so that a harmonic current entering a voltage adjustment module is stable. A frequency converter is externally connected to a first-stage inductance, and noise waves and high-frequency high-order harmonic waves of a power source are effectively filtered, so that a fault that the frequency converter and a voltage adjustment module are burn out since the frequency converter and the voltage adjustment module are directly connected to loads is resolved, and high-order harmonic waves fed back in a process of driving plasma to discharge may be also filtered, thereby ensuring stable operation of an entire loop. The voltage adjustment module is backward connected to a second-stage inductance, so that generation of a negative resistance effect in a plasma charging process is avoided when a voltage of a circuit is adjusted and changed, thereby causing an output voltage more stable, and a system can operate reliably for a long time.

In addition, a high-voltage electric field low-temperature plasma cold sterilization apparatus is provided, including the high-voltage electric field low-temperature plasma cold sterilization system circuit, and an objective of performing efficient cold sterilization on packaged food by generating space plasma in conditions of a large area, a large gap, and a large atmosphere is achieved.

Technical solutions

To achieve the foregoing objective, the present invention provides the following technical solutions:

The present invention provides a high-voltage electric field low-temperature plasma cold sterilization system circuit, including a power source module configured to output a harmonic current, a voltage adjustment module configured to adjust a load voltage, a current, and power, a switch module configured to adjust a switch-on and switch-off state of a circuit, and a transformer power supply module configured to generate a high voltage, where the power source module includes a frequency converter and a first-stage inductance, the frequency converter includes an input end, an output end T1, and an output end T3, the input end is connected to a single-phase alternating current power source, the output end T3 is connected to the voltage adjustment module, and the output end T1 is connected to the first-stage inductance, so that harmonic components in sine pulse width modulation (SPWM) waves outputted by the frequency converter may be effectively restrained, spectrum is expanded, a harmonic current entering the voltage adjustment module is stable, and heat losses of the voltage adjustment module are reduced to prevent burnout;

the voltage adjustment module includes an input end A and an input end X, the input end A of the voltage adjustment module is connected to the first-stage inductance, and the input end X is connected to the output end T3; and the voltage adjustment module includes an output end a and an output end x, and the output end a and the output end x are connected to the switch module;

the switch module includes an input end L1$a$ and an input end L3$a$, the input end L1$a$ is connected to the output end a of the voltage adjustment module, and the input end L3$a$ is connected to the output end x of the voltage adjustment module; and the switch module includes an output end U1 and an output end U3, the output end U1 and the output end U3 are connected to the power supply module; and the power supply module includes an input end L1$c$ and an input end L3$c$, the input end L1$c$ is connected to the output end U1 of the switch module, and the input end L3$c$ is connected to the output end U3 of the switch module; and the power supply module includes four output ends, and the output ends are connected to loads.

As a further improvement of the present invention, the frequency converter is a single-phase frequency converter, the single-phase frequency converter includes an input end L1 and an input end L3, and the input end L1 and the input end L3 are connected to a single-phase alternating current power source. An input of a single-phase alternating current (AC220) may be adapted.

As a further improvement of the present invention, the frequency converter is a three-phase frequency converter, the three-phase frequency converter includes an input end L1, an input end L2, and an input end L3, and the input end L1, the input end L2, and the input end L3 are connected to a three-phase alternating current power source. An input of a three-phase alternating current (AC380) can be adapted.

As a further improvement of the present invention, the voltage adjustment module includes an electric voltage regulator and a second-stage inductance, where the electric voltage regulator includes an input end A and an input end X, the input end A of the electric voltage regulator is connected to the first-stage inductance, and the input end X of the electric voltage regulator is connected to the output end T3 of the single-phase frequency converter; and the electric voltage regulator includes an output end a and an output end x, the output end a of the electric voltage regulator is connected to one end of the second-stage inductance, the voltage regulator is backward connected to the second-stage inductance, thereby avoiding generation of a negative resistance effect when a voltage of a circuit is adjusted and changed, and causing an output voltage to be stable. The other end of the second-stage inductance is connected to the switch module, and the output end x of the electric voltage regulator is connected to the switch module. The output ends of the electric voltage regulator are filtered again through the inductance, which is more beneficial to effectively restraining the harmonic components.

As a further improvement of the present invention, the switch module includes an alternating current contactor and a solid state relay, where the alternating current contactor includes at least six contacts; the solid state relay includes an input end L1$b$ and an input end L3$b$, and an output end U1 and an output end U3; the input end L1$a$ of the switch module is a contact 1 of the alternating current contactor, the input end L3$a$ of the switch module is a contact 5 of the alternating current contactor, the contact 1 of the alternating current contactor is connected to the second-stage inductance, and the contact 5 of the alternating current contactor is connected to the output end of the electric voltage regulator; a contact 2 of the alternating current contactor is connected to the input end L1$b$ of the solid state relay, and the contact 6 of the alternating current contactor is connected to the input end L3$b$ of the solid state relay; the contact 3 and a contact 4 of the alternating current contactor are on standby; and the output end U1 and the output end U3 of the solid state relay are connected to the power supply module. The solid state relay plays a role of full isolation in the circuit as a non-contact switch to reduce interference, so that a service life is increased and working stability is improved. Therefore, in a circuit loop, a format that a pulse power source supplies power may be formed.

As a further improvement of the present invention, the power supply module includes a first transformer, the output end U1 and the output end U3 of the solid state relay are connected to two ends of a primary coil of the first transformer respectively, and an output end of a secondary coil of the first transformer is connected to a load.

As a further improvement of the present invention, the power supply module further includes a second transformer, and the first transformer and the second transformer are connected in parallel. Consistency of input voltages of the two transformers may be ensured through parallel connection.

As a further improvement of the present invention, the power supply module includes at least two transformers, and the transformers are connected in parallel, to adapt to a requirement of a plurality of loads.

As a further improvement of the present invention, a capacitor is connected in parallel between the output end T1 and the output end T3 of the single-phase frequency converter. Therefore, a filtering effect is further improved.

The present invention provides a high-voltage electric field low-temperature plasma cold sterilization apparatus, including a housing and the high-voltage electric field low-temperature plasma cold sterilization system circuit, where the high-voltage electric field low-temperature plasma cold sterilization system circuit is mounted inside the housing.

Beneficial Effects

Compared with the existing technologies, the technical solutions provided in the present invention have the following beneficial effects:

According to the high-voltage electric field low-temperature plasma cold sterilization system circuit of the present invention, an output voltage of the power source module is controllable, the harmonic components in the outputted SPWM waves are effectively restrained, and the spectrum is expanded, so that a harmonic current entering the voltage adjustment module is stable. The voltage regulator is backward connected to the second-stage inductance, thereby avoiding generation of a negative resistance effect when a voltage of a circuit is adjusted and changed, and causing an output voltage to be stable. According to the high-voltage electric field low-temperature plasma cold sterilization apparatus of the present invention, the high-voltage electric field low-temperature plasma cold sterilization system circuit is included, a structure design is appropriate, the principle is simple, and the apparatus is easy to promote and use.

Figure 1:
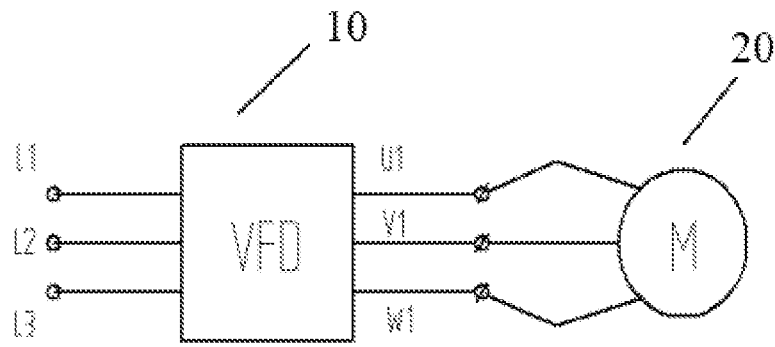
FIG. 1 is a schematic wiring diagram of a motor controlled by a conventional frequency converter.

Descriptions of reference numerals in the schematic diagrams:

10. Frequency converter; 20. Motor; 100. Power source module; 110. Single-phase frequency converter; 120. First-stage inductance; 130. Three-phase frequency converter; 200. Voltage adjustment module; 210. Electric voltage regulator; 220. Second-stage inductance; 300. Switch module; 310. Alternating current contactor; 320. Solid state relay; 400. Power supply module; 410. First transformer; 420. Second transformer.

DETAILED DESCRIPTION

To further understand the content of the present invention, the present invention is described in detail with reference to the accompanying drawings and embodiments.

The structures, proportions, sizes, and the like shown in the drawings of this specification, in coordination with the content disclosed in this specification, are only used to help a person skilled in the art to read and understand, and they are not intended to limit the conditions under which the present invention can be implemented and therefore have no technical significance. Any modification to the structures, change to the proportional relationships, or adjustment on the sizes should fall within the scope of the technical content disclosed by the present invention without affecting the effects and the objectives that can be achieved by the present invention. In addition, terms such as "upper", "lower", "left", "right", and "middle" mentioned in this specification are also merely for facilitating clear descriptions, but are not intended to limit the scope of implementation. Without substantially changing the technical contents, changes or adjustments of relative relationships thereof should also fall within the scope of implementation of the present invention.

Referring to FIG. 1, FIG. 1 is a diagram of a circuit used by a conventional frequency converter to connect to a motor, where a frequency converter 10 and a motor 20 are included, and a conventional working principle is not described herein again.

The present invention is further described below with reference to embodiments.

Embodiment 1

Figure 2:
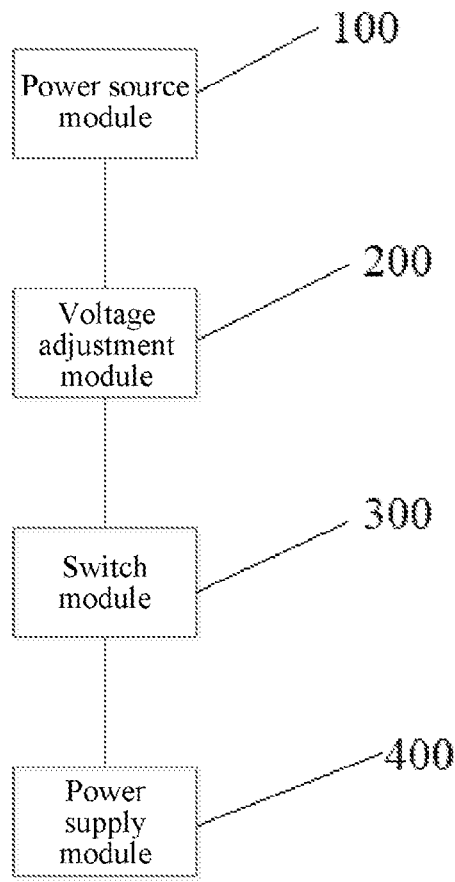
FIG. 2 is module diagram of the present invention.

Referring to FIG. 2, FIG. 2 is a module diagram of a high-voltage electric field low-temperature plasma cold sterilization system circuit of the present invention.

A high-voltage electric field low-temperature plasma cold sterilization system circuit is provided, including a power source module 100 configured to output a harmonic current, a voltage adjustment module 200 configured to adjust a load voltage, a current, and power, a switch module 300 configured to adjust a switch-on and switch-off state of a circuit, and a transformer power supply module 400 configured to generate a high voltage.

The power source module 100 may be externally connected to a single-phase power source input or a three-phase power source input, and output a single-phase voltage. An output voltage of the power source module 100 is controllable, harmonic components in an outputted SPWM waves are effectively restrained, and spectrum is expanded, so that a harmonic current entering the voltage adjustment module 200 is stable.

The power source module 100 includes two or three power source input ends. Specifically, when a single-phase power source (such as AC220) is used, the power source module 100 includes two power source input ends; and when a three-phase power source (such as AC380) is used, the power source module 100 includes three power source input ends. The power source module 100 includes two output ends, and the output ends are connected to the voltage adjustment module 200.

The voltage adjustment module 200 is connected between the power source module 100 and a load, to adjust a voltage, a current, and power applied to the load. An output voltage of the voltage adjustment module 200 is controllable.

The voltage adjustment module 200 includes two input ends, and the input ends are connected to the output ends of the power source module 100. The voltage adjustment module 200 includes two output ends, and the output ends are connected to the switch module 300.

The switch module 300 is connected between the voltage adjustment module 200 and the power supply module 400, to control switch-on and switch-off of a circuit. In addition, the switch module may isolate the power source module 100, the voltage adjustment module 200, and the power supply module 400, thereby reducing mutual interference, and improving service lives.

The switch module 300 includes two input ends, and the input ends are connected to the voltage adjustment module 200. The switch module 300 includes two output ends, and the output ends are connected to the power supply module 400.

Preferably, the switch module 300 may control the switch-on and switch-off of the circuit in an automatic control manner.

The power supply module 400 is a working part of the present invention, is configured to supply power to a high-voltage electric field low-temperature plasma generation circuit, and may generate a high voltage.

The power supply module 400 includes two input ends, and the input ends are connected to the switch module 300. The power supply module 400 includes four output ends, and the output ends are connected to a low-temperature plasma discharging unit (not shown in the figure).

Preferably, a quantity of output ends of the power supply module 400 may be adjusted as required.

Embodiment 2

Figure 3:
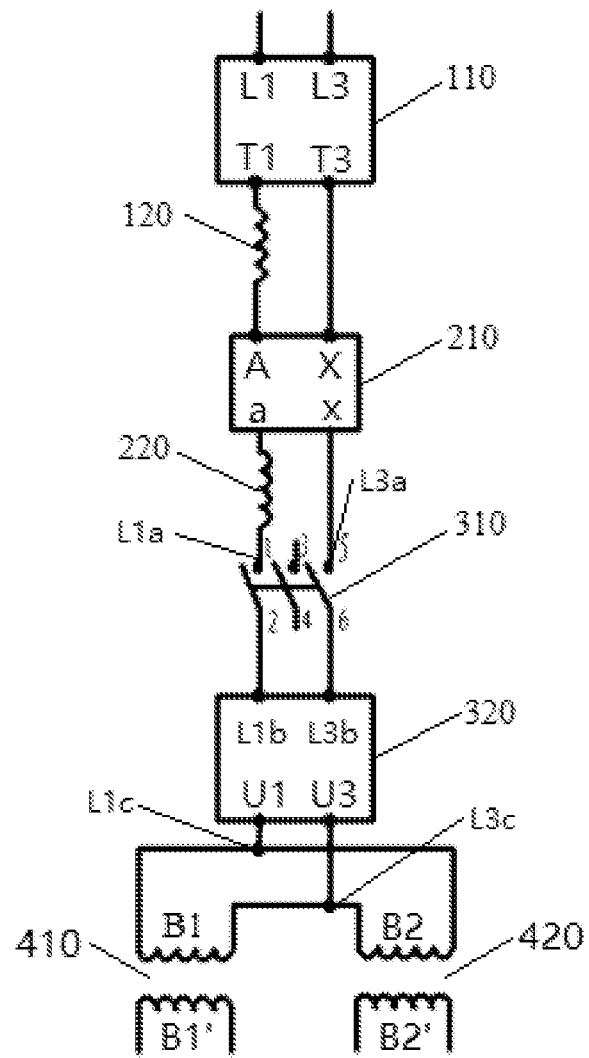
FIG. 3 is a circuit principle diagram of the present invention.

Referring to FIG. 3, FIG. 3 is a circuit diagram of a high-voltage electric field low-temperature plasma cold sterilization system circuit. In the high-voltage electric field low-temperature plasma cold sterilization system circuit of this embodiment, the power source module 100 includes a single-phase frequency converter 110, the single-phase frequency converter 110 includes two input ends connected to a single-phase power source (such as AC220), an output end T1 of the single-phase frequency converter 110 is connected to one end of a first-stage inductance 120, the other end of the first-stage inductance 120 is connected to the voltage adjustment module 200, and an output end T3 of the single-phase frequency converter 110 is connected to the voltage adjustment module 200. As required, a capacitor may be connected in parallel between the two output ends T1 and T3 of the single-phase frequency converter 110, to enhance a filtering effect.

Still referring to FIG. 3, the voltage adjustment module 200 includes an electric voltage regulator 210, the electric voltage regulator 210 includes two input ends, an input end A of the electric voltage regulator 210 is connected to the first-stage inductance 120, and an input end X of the electric voltage regulator 210 is connected to the output end T3 of the single-phase frequency converter 110. The electric voltage regulator 210 includes two output ends, an output end a of the electric voltage regulator 210 is connected to one end of a second-stage inductance 220, the other end of the second-stage inductance 220 is connected to the switch module 300, and an output end x of the electric voltage regulator 210 is connected to the switch module 300.

Preferably, inductive reactance of the second-stage inductance=$(1\sim1.5)\times$(capacitive reactance of the load at a static moment$\times 10^3$), and inductive reactance of the first-stage inductance=$(0.5\sim2)\times$the inductive reactance of the second-stage inductance.

Still referring to FIG. 3, the switch module 300 includes an alternating current contactor 310 and a solid state relay 320. The alternating current contactor 310 includes at least six contacts, and the solid state relay 320 includes two input ends and two output ends. A contact 1 of the alternating current contactor 310 is connected to the second-stage inductance 220, a contact 5 of the alternating current contactor 310 is connected to the output end x of the electric voltage regulator 210, a contact 2 of the alternating current contactor 310 is connected to an input end L1$b$ of the solid state relay 320, a contact 6 of the alternating current contactor 310 is connected to an input end L3$b$ of the solid state relay 320, and a contact 3 and a contact 4 of the alternating current contactor 310 are on standby. For the sake of security, the foregoing contacts are all normally open contacts. Preferably, the alternating current contactor 310 may control switch-on and switch-off states of the contacts in an automatic control manner. For example, a power source and coil contacts of the alternating current contactor 310 are connected to form a loop by using output signals and output communications (COM) ports of a programmable logic controller (PLC), and whether coils of the alternating current contactor 310 are powered on may be controlled through outputs of a switch quantity. An output end U1 and an output end U3 of the solid state relay 320 are connected to the power supply module 400. Outputs of existing power sources are generally in a continuous waveform, and intermittent discharging may be implemented after the alternating current contactor 310 and the solid state relay 320 are used, to form intermittent discharging in a time domain, so as to form a pulse waveform.

Referring to FIG. 3, the power supply module 400 includes a first transformer 410 and a second transformer 420, and the first transformer 410 and the second transformer 420 are connected in parallel, thereby ensuring consistency of input voltages of two ends of the first transformer 410 and the second transformer 420. The output end U1 of the solid state relay 320 is connected to an input end L1$c$ of the first transformer 410, and the output end U3 of the solid state relay 320 is connected to an input end L3$c$ of the second transformer 420, and primary coils of the first transformer 410 and the second transformer 420 are connected in parallel. Output ends of secondary coils of the first transformer 410 and the second transformer 420 are connected to loads respectively.

Preferably, a quantity of the transformers may be greater than 2 and may be set as required.

Embodiment 3

Figure 4:
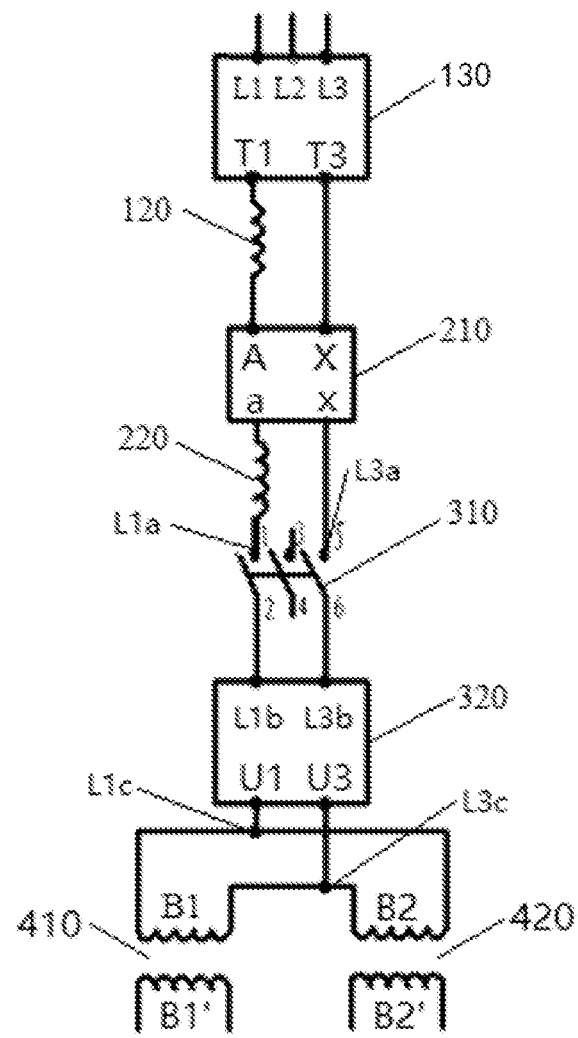
FIG. 4 is a circuit principle diagram of the present invention.

Referring to FIG. 4, in the high-voltage electric field low-temperature plasma cold sterilization system circuit of this embodiment, a basic circuit connection manner is the same as that of embodiment 2, and improvements lie in that:

The power source module 100 includes a three-phase frequency converter 130, the three-phase frequency converter 130 includes three input ends connected to a three-phase power source (such as AC380), an output end T1 of the three-phase frequency converter 130 is connected to one end of a first-stage inductance 120, the other end of the first-stage inductance 120 is connected to the voltage adjustment module 200, and an output end T3 of the three-phase frequency converter 130 is connected to the voltage adjustment module 200. As required, a capacitor may be connected in parallel between the two output ends T1 and T3 of the three-phase frequency converter 130, to enhance a filtering effect. Using a three-phase frequency converter may be suitable for a case that extension is required and more loads need to be connected, and certainly, is not merely limited to this case.

Still referring to FIG. 4, the voltage adjustment module 200 includes an electric voltage regulator 210, the electric voltage regulator 210 includes two input ends, an input end A of the electric voltage regulator 210 is connected to the first-stage inductance 120, and an input end X of the electric voltage regulator 210 is connected to the output end T3 of the three-phase frequency converter 130. The electric voltage regulator 210 includes two output ends, an output end a of the electric voltage regulator 210 is connected to one end of a second-stage inductance 220, the other end of the second-stage inductance 220 is connected to the switch module 300, and an output end x of the electric voltage regulator 210 is connected to the switch module 300.

Embodiment 4

Referring to FIG. 3 and FIG. 4, the high-voltage electric field low-temperature plasma cold sterilization system circuit of Embodiment 2 or Embodiment 3 is used, and a working principle of this embodiment is that:

A single-phase alternating current is inputted into a power source input end of the single-phase frequency converter 110, or a three-phase alternating current is inputted into a power source input end of the three-phase frequency converter 130. An output end of the single-phase frequency converter 110 or the three-phase frequency converter 130 outputs single-phase alternating sine pulse width modulation (SPWM) waves, pulse width modulation harmonic waves outputted by the single-phase frequency converter 110 or the three-phase frequency converter 130 are filtered and effectively restrained through the first-stage inductance 120, and spectrum is expanded, so that a harmonic current entering a primary coil of the electric voltage regulator 210 is stable, heat losses and burnout of coils of the electric voltage regulator 210 may be reduced, and a case that the frequency converter is used as an input power source of the electric voltage regulator 210 is implemented.

A range f of output frequencies of the frequency converter is from 50 Hz to 200 Hz. An output voltage of the electric voltage regulator 210 is filtered by the second-stage inductance 220, and enters the input end of the solid state relay 320 through the alternating current contactor 310 (contact closing conditions are controlled). When the solid state relay 320 receives intermittently triggered voltage signals, the on-off of the solid state relay 320 is performed according to a specific frequency, to play a role of protecting ends from high voltage discharging and heat dissipation controlling. When a pulse voltage at a specific frequency enters primary coil loops B1 and B2 of the first transformer 410 and the second transformer 420, due to the electromagnetic induction principle, secondary coils B1' and B2' generate high voltages to drive loads.

Embodiment 5

A high-voltage electric field low-temperature plasma cold sterilization apparatus is provided, using the high-voltage electric field low-temperature plasma cold sterilization system circuit of Embodiment 1, Embodiment 2, or Embodiment 3, and including a housing, where the high-voltage electric field low-temperature plasma cold sterilization system circuit is disposed inside the housing.

A form of the housing is disposed according to the layout of high-voltage electric field low-temperature plasma cold sterilization system circuit, and may include a bottom surface and three side surfaces, where one side surface is opened for ease of circuit mounting and maintenance.

It should be noted that, fields to which the present invention may be applied is not merely limited to the food field, and the present invention may be further applied to fields such as medical equipment and books and newspapers where sterilization and disinfection are required.

The foregoing exemplarily describes the present invention and implementations thereof, and is not restrictive. The accompanying drawings only show one of the implementations of the present invention, and the actual structure is not limited thereto. Therefore, similar structures and embodiments designed by a person of ordinary skill in the art as inspired by the disclosure herein without departing from the spirit of the present invention and without creative efforts shall fall within the protection scope of the present invention.

What is claimed is:

1. A high-voltage electric field low-temperature plasma cold sterilization system circuit, comprising a power source module configured to output a harmonic current, a voltage adjustment module configured to adjust a load voltage, a current, and power, a switch module configured to adjust a switch-on and switch-off state of a circuit, and a transformer power supply module configured to generate a high voltage, wherein the power source module comprises a frequency converter and a first-stage inductance, the frequency converter comprises an input end and output ends T1 and T3, the input end is connected to an alternating current power source, the output end T3 is connected to the voltage adjustment module, and the output end T1 is connected to the first-stage inductance;

the voltage adjustment module comprises an input end A and an input end X, the input end A of the voltage adjustment module is connected to the first-stage inductance, and the input end X is connected to the output end T3; and the voltage adjustment module comprises an output end a and an output end x, and the output end a and the output end x are connected to the switch module;

the switch module comprises an input end L1a and an input end L3a, the input end L1a is connected to the output end a of the voltage adjustment module, and the input end L3a is connected to the output end x of the voltage adjustment module; and the switch module comprises an output end U1 and an output end U3, and the output end U1 and the output end U3 are connected to the power supply module; and the power supply module comprises an input end L1c and an input end L3c, the input end L1c is connected to the output end U1 of the switch module, and the input end L3c is connected to the output end U3 of the switch module; and the power supply module comprises four output ends, and the output ends are connected to loads.

2. The high-voltage electric field low-temperature plasma cold sterilization system circuit according to claim 1, wherein the frequency converter is a single-phase frequency converter, the single-phase frequency converter comprises an input end L1 and an input end L3, and an output end T1 and an output end T3, and the input end L1 and the input end L3 are connected to a single-phase alternating current power source.

3. The high-voltage electric field low-temperature plasma cold sterilization system circuit according to claim 1, wherein the frequency converter is a three-phase frequency converter, the three-phase frequency converter comprises an input end L1, an input end L2, and an input end L3, and an output end T1 and an output end T3, and the input end L1, the input end L2, and the input end L3 are connected to a three-phase alternating current power source.

4. The high-voltage electric field low-temperature plasma cold sterilization system circuit according to claim 1, wherein the voltage adjustment module comprises an electric voltage regulator and a second-stage inductance, wherein the electric voltage regulator comprises an input end A and an input end X, the input end A of the electric voltage regulator is connected to the first-stage inductance, and the input end X of the electric voltage regulator is connected to the output end T3 of the single-phase frequency converter; and the electric voltage regulator comprises an output end a and an output end x, the output end a of the electric voltage regulator is connected to one end of the second-stage inductance, the other end of the second-stage inductance is connected to the switch module, and the output end x of the electric voltage regulator is connected to the switch module.

5. The high-voltage electric field low-temperature plasma cold sterilization system circuit according to claim 4, wherein the switch module comprises an alternating current contactor and a solid state relay, wherein the alternating current contactor comprises at least six contacts; the solid state relay comprises an input end L1*b* and an input end L3*b*, and an output end U1 and an output end U3; the input end L1*a* of the switch module is a contact 1 of the alternating current contactor, the input end L3*a* of the switch module is a contact 5 of the alternating current contactor, the contact 1 of the alternating current contactor is connected to the second-stage inductance, and the contact 5 of the alternating current contactor is connected to the output end of the electric voltage regulator; a contact 2 of the alternating current contactor is connected to the input end L1b of the solid state relay, and the contact 6 of the alternating current contactor is connected to the input end L3*b* of the solid state relay; the contact 3 and a contact 4 of the alternating current contactor are on standby; and the output end U1 and the output end U3 of the solid state relay are connected to the power supply module.

6. The high-voltage electric field low-temperature plasma cold sterilization system circuit according to claim 5, wherein the power supply module comprises a first transformer, the output end U1 and the output end U3 of the solid state relay are connected to two ends of a primary coil of the first transformer respectively, and an output end of a secondary coil of the first transformer is connected to a load.

7. The high-voltage electric field low-temperature plasma cold sterilization system circuit according to claim 6, wherein the power supply module further comprises a second transformer, and the first transformer and the second transformer are connected in parallel.

8. The high-voltage electric field low-temperature plasma cold sterilization system circuit according to claim 7, wherein the power supply module comprises at least two transformers, and the transformers are connected differentially.

9. The high-voltage electric field low-temperature plasma cold sterilization system circuit according to claim 1, wherein a capacitor is connected in parallel between the output end T1 and the output end T3 of the single-phase frequency converter.

10. A high-voltage electric field low-temperature plasma cold sterilization apparatus, comprising a housing and the high-voltage electric field low- temperature plasma cold sterilization system circuit according to claim 1, wherein the high-voltage electric field low-temperature plasma cold sterilization system circuit is mounted inside the housing.

* * * * *